(12) United States Patent
Azarnia et al.

(10) Patent No.: US 7,378,270 B2
(45) Date of Patent: May 27, 2008

(54) DEVICE FOR ANALYTE MEASUREMENT

(75) Inventors: Roobik Azarnia, South Miami, FL (US); James W. Walker, Miami Lakes, FL (US)

(73) Assignee: Sentec Scientific, Inc., Homestead, FL (US)

( * ) Notice: Subject to any disclaimer, the term of this patent is extended or adjusted under 35 U.S.C. 154(b) by 634 days.

(21) Appl. No.: 10/984,599

(22) Filed: Nov. 9, 2004

(65) Prior Publication Data

US 2005/0214881 A1 Sep. 29, 2005

Related U.S. Application Data

(60) Provisional application No. 60/518,828, filed on Nov. 10, 2003.

(51) Int. Cl.
*C12M 1/34* (2006.01)
*C12M 3/00* (2006.01)

(52) U.S. Cl. ............... 435/287.2; 435/7.92; 435/287.3; 436/515; 422/82.05

(58) Field of Classification Search ............ 435/287.2, 435/287.3, 7.92; 422/82.05; 221/87; 436/514
See application file for complete search history.

(56) References Cited

U.S. PATENT DOCUMENTS

| | | | |
|---|---|---|---|
| 3,620,678 A * | 11/1971 | Guigan et al. ................. 422/66 |
| 4,071,315 A * | 1/1978 | Chateau ....................... 436/518 |
| 4,218,421 A | 8/1980 | Mack, Jr. et al. |
| 4,512,952 A | 4/1985 | Blanding et al. |
| 4,871,439 A | 10/1989 | Enzer et al. |
| 4,878,971 A * | 11/1989 | Tsunekawa et al. ........... 156/70 |
| 4,883,642 A * | 11/1989 | Bisconte ....................... 422/66 |
| 4,935,346 A | 6/1990 | Phillips et al. |
| 5,004,582 A | 4/1991 | Miyata et al. |
| 5,059,393 A | 10/1991 | Quenin et al. |
| 5,077,010 A | 12/1991 | Ishizaka et al. |
| 5,096,836 A | 3/1992 | Macho et al. |
| 5,120,506 A * | 6/1992 | Saito et al. ................... 422/66 |
| 5,143,694 A | 9/1992 | Schafer et al. |
| 5,178,835 A | 1/1993 | Uekusa et al. |

(Continued)

FOREIGN PATENT DOCUMENTS

WO  WO2004/047642  6/2004

(Continued)

*Primary Examiner*—Walter D. Griffin
*Assistant Examiner*—Shanta G Doe
(74) *Attorney, Agent, or Firm*—Howard Gitten; Edwards Angell Palmer & Dodge LLP (57) ABSTRACT

A biochemical analysis instrument for multiple fluid analyses includes a housing. A sensor for sensing a reaction is disposed in the housing. An aperture is formed in the housing. A test tape housing area is formed in the housing, and the sensor is disposed to selectively move within the housing area; the aperture being formed to provide access to the tape housing area. A cassette is configured to be received within the tape housing area. The cassette includes a case. First and second chambers are formed in the case. A gap is formed in the case. The first chamber and second chamber are disposed at a respective side of the gap. A test tape disposed within the housing extends from the first chamber across the gap to the second chamber. The test tape includes a plurality of active zones disposed at predetermined spaced intervals along the tape for testing an analyte.

22 Claims, 10 Drawing Sheets

U.S. PATENT DOCUMENTS

| | | |
|---|---|---|
| 5,284,568 A | 2/1994 | Pace et al. |
| 5,447,690 A | 9/1995 | Sugaya |
| 5,471,270 A | 11/1995 | Balling |
| 5,534,224 A | 7/1996 | Abe |
| 5,582,698 A | 12/1996 | Flaherty et al. |
| 5,599,505 A | 2/1997 | Fujisaki et al. |
| 5,632,410 A | 5/1997 | Moulton et al. |
| 5,665,310 A | 9/1997 | Augstein |
| 5,686,047 A | 11/1997 | Augstein |
| 5,824,491 A * | 10/1998 | Priest et al. .................. 435/28 |
| 5,846,490 A | 12/1998 | Yokota et al. |
| 5,854,074 A | 12/1998 | Charlton et al. |
| 2002/0188224 A1* | 12/2002 | Roe et al. .................... 600/584 |
| 2004/0258564 A1* | 12/2004 | Charlton ...................... 422/58 |
| 2006/0216817 A1* | 9/2006 | Hoenes et al. ........... 435/287.2 |

FOREIGN PATENT DOCUMENTS

WO     WO2004/056269     7/2004

* cited by examiner

DEVICE FOR ANALYTE MEASUREMENT

CROSS-REFERENCE TO RELATED APPLICATIONS

This Application claims priority from U.S. Provision Application No. 60/518,828, entitled DEVICE FOR ANALYTE MEASUREMENT filed on Nov. 10, 2003.

BACKGROUND OF THE INVENTION

1. Field of Invention

The present invention generally relates to a novel disposable test tape cassette for measuring the concentration of analytes in a fluid sample, and more specifically, to a continuous band of sensor test tape capable of analyzing glucose in a small sample of whole blood. The invention also provides an analysis device capable of receiving, dispensing and analyzing the test tape cassette.

2. Background

Detection and measurement of an appropriate analyte(s) in a small sample of blood or other biological fluid samples, at home or near the patient has become commonplace in clinical medicine and is aiding in the diagnosing, monitoring and treatment of many diseases. One prominent example of this practice is the way diabetics are able to self-monitor and control their blood glucose to near normal levels at home or at work. This type of self-monitoring and good control significantly reduces the risk of developing serious complications related to diabetes as shown by landmark outcome studies.

Good control, among other steps to be taken by the patient, requires routine self-monitoring of blood glucose levels at several daily intervals. Beginning in the early 1970's, relatively easy-to-use self monitoring devices provided blood glucose measurements by diabetics, allowing better control of blood glucose levels by utilizing the test results to determine proper insulin dosage or other medications to be administered. Early models of such blood glucose monitoring (BGM) devices were based on photometric principles of glucose detection, whereas more recent devices are biosensor (e.g. electrochemical) based in their operation.

In both versions of the BGM devices, generally a disposable, one-time-use reagent test strip is used in conjunction with the analysis device. Such test strips are generally small, flat and rectangular with the two ends serving separate functions. All such strips have a front end to receive a small volume of capillary blood from a finger stick. In addition, the front end contains an appropriate reagent mixture that reacts chemically with the analyte present in the blood sample, in this case glucose, to generate an appropriate signal; either a color change or an electrochemical signal proportional to the amount of analyte present in the fluid sample. In the optical BGM devices, the end result of the chemical reaction is a color change detected and measured, whereas in the biosensor based BGM devices there is an electrochemical reaction taking place resulting in an electrical signal detected and measured. The other end of the test strip is to be inserted into the BGM device to position the test strip in the appropriate place within the device for optical measurement or in the case of biosensor based devices, to make electrical contact for the electrodes built into the strips with the electrical circuitry built into the analysis device to receive electrical signals.

With any of the existing BGM devices, the patient or the end user must unwrap or unzip the metallic foil containing the test strip, or alternatively in certain brands open the top of a tightly fitted container and retrieve a single test strip every time, then make certain that the strip is inserted properly with the correct side up and the correct end in the slot provided in the device. Following a measurement taken from a sample of blood, the test strip must be removed and discarded safely and properly along with the cover foil.

There are a number of inherent disadvantages to the existing strips.

1. The user must always carry an adequate number of test trips in a separate container from the analysis device.

2. Many of the existing test strips are wrapped individually within some kind of metallic foil. The opening and the unwrapping of most of these metallic wrappers for the retrieval of the individual test strip require considerable effort and force. This is especially difficult to perform for many younger patients who constitute a large portion of the Type I diabetics and also for some older or seriously ill patients.

3. Safe and clean retrieval and disposal of the test strip contaminated with blood at the completion of the test adds additional time and effort to the self monitoring process and represents a potential source of health hazard.

4. The manufacturing process for these test strips is elaborate and costly. In the case of the biosensor-based strips, the process requires additional steps and components for incorporating electrodes into the test strips, hence increasing overall cost.

In recent years as described in U.S. Pat. No. 5,854,074, there has been developed and put into practice for use by diabetics and others, a sensor pack disposed in a housing of a sensor dispensing instrument capable of handling a plurality of individual test strips used one at a time and discarded after each use. The cartridge holds a limited number of strips, therefore limiting the number of tests per cartridge to no more than ten, and again each blood covered strip must be disposed of after use, creating a potential bio-hazard.

In a separate development a long-test-film cassette for an automated biochemical analysis instrument capable of handling fluid samples and multiple tests for each fluid sample is described in U.S. Pat. No. 5,077,010. The analysis instrument is designed for use in a clinical laboratory for testing many fluid samples for multiplicity of tests and requires proper refrigeration of the unused portion of the test film and incubation of said test film once a fluid sample is delivered to the test film.

There remains a need in the art for an apparatus and for a more convenient and less costly method of self-monitoring of blood glucose. The method should yield a user-friendlier means of measuring blood glucose at home or at the workplace.

BRIEF SUMMARY OF THE INVENTION

The present invention includes a fluid sensing device and apparatus capable of receiving, dispensing and analyzing a continuous band of test tape, which test tape is enclosed within a housing, in the form of a cassette, and wherein the cassette includes an exposed test zone open to the ambient space capable of receiving a small sample of blood. The test tape is selectively exposed at the test zone. The tape includes at least one exposed active zone of the test tape, and whereby the test tape is in contact with or in close proximity of an electrochemical or optical sensor means.

According to an aspect of the present invention there is provided a test tape suitable for use in a test device for testing of analyte concentration in a fluid to be applied thereto, the test tape includes a base layer having an active zone to which the fluid sample is to be applied. The active zone contains reagents which are specific and reactive to the analyte to produce an electrochemical signal or a color change proportional to the amount of the analyte present in the fluid sample. Furthermore, the tape includes a cleansing zone adjacent the active zone for the purpose of cleaning and/or cleansing of an electrode surface of the fluid sensing device in preparation for a subsequent test. Such cleansing zone may not be required for the optical methods of detecting a color change from the addition of a sample of the fluid containing the analyte of interest.

The test tape may be of any desired chemical composition or make-up, thickness, width and made up of plurality of layers, if so desired, for a particular application. However, typically the test tape will be an elongate tape capable of multiple tests; preferably as many as one hundred or more tests for a given analyte of interest. However, it is to be understood that the invention is not limited to this embodiment alone. The test tape may be constructed such that it may provide the ability to test the presence of other analytes of interest in a fluid sample. Examples of other analytes include, and are not limited to, cholesterol, creatinine, alcohols, and any chemical or biological substance of interest for medical, industrial or other test applications.

In one embodiment, the reagent is specific for and is reactive to the analyte to produce a visible color change. Alternatively, the reagent may react with the analyte to produce an electrochemical signal, which is measured and displayed by the device. In this embodiment, the opposite side of the test tape to the active zone is in electrical contact with the electrodes of the device. The invention will be described hereinafter with reference to this embodiment.

To construct the active zone, a plurality of operational members may be sequentially applied to a base layer by a variety of methods. For example, the members may be applied by dot blotting, screen printing, inkjet or similar methods of dispersing liquids or gels onto the surfaces of tapes, membranes or bands.

In a preferred embodiment of the present invention, at least a segment of the cleansing zone may be made thicker or more absorbent than the active zone by any suitable means. Suitable means may include other components and/or chemicals capable of adsorbing or absorbing material in general, chemical end products from the chemical reaction between the analyte of interest and the reagent present in the active zone, or from the sample introduced to the active zone, that may have been deposited onto the surface of the electrochemical sensor during the course of the analysis.

The invention also provides a test device or apparatus, which is capable of receiving, dispensing and analyzing a test tape. Accordingly, an aspect of the present invention provides a test apparatus for testing of analyte concentration in a fluid to be applied thereto, the device including a continuous test tape having a plurality of active zones sequentially disposed thereon, each active zone carrying reagent means for producing an electrical signal or a color change in response to the concentration of analyte in an applied fluid sample. Each active zone having a base layer to which the fluid sample is to be applied, the base layer containing the reagent means. A plurality of cleansing zones is intermittently disposed along the tape adjacent a respective active zone for the purpose of cleansing the electrochemical electrode surfaces. In another aspect of the present invention, a cleansing zone need not follow the active zone when the sensing mode is that of an optical sensor.

A test tape cassette housing is made of moldable plastic material of ordinary type, and includes two chambers. The first chamber contains the unused test tape and the second chamber receives the used portion of the test tape that it receives in predetermined short segments with each measurement. When the test tape is completely used up, the entire cartridge is removed from the measuring device and discarded. The unused and used test tape chambers are sealed airtight and may in addition contain desiccant material to maintain low humidity within the chambers.

The test tape may be sequentially displaced in a single step fashion, by appropriate mechanical means built into the housing from the unused chamber to the test zone in order to receive the next fluid sample.

The cassette is adapted to be received in an analysis device. A sensor head built into the dispensing and analysis device contains electrodes built into its structure capable of making physical contact with the test tape as it passes through the test zone and detecting electrochemical signals generated by the chemical reaction of the reagent with the fluid sample. Furthermore, in one embodiment the sensor head is capable of vertical movement within the dispensing and analysis device. During a test procedure the sensor head is raised to an upper position making intimate physical contact with the test tape and forcing the test tape to take on a inverted U shape protruding from the upper portion of the dispensing and analysis device and capable of receiving a small volume of fluid sample, for example a small drop of blood sample directly applied by the touch of a finger tip. In yet another embodiment of the present invention, the electrochemical sensor head remains stationary and is in physical contact with the test tape at all times. In a separate embodiment of the present invention, the sensor head is of optical nature, is located at close proximity of the test tape, and need not be in physical contact with the test tape.

BRIEF DESCRIPTION OF THE DRAWINGS

For a fuller understanding of the invention, reference is had to the following description taken in connection with the accompanying drawings in which.

DETAILED DESCRIPTION OF THE INVENTION

Figure 1:
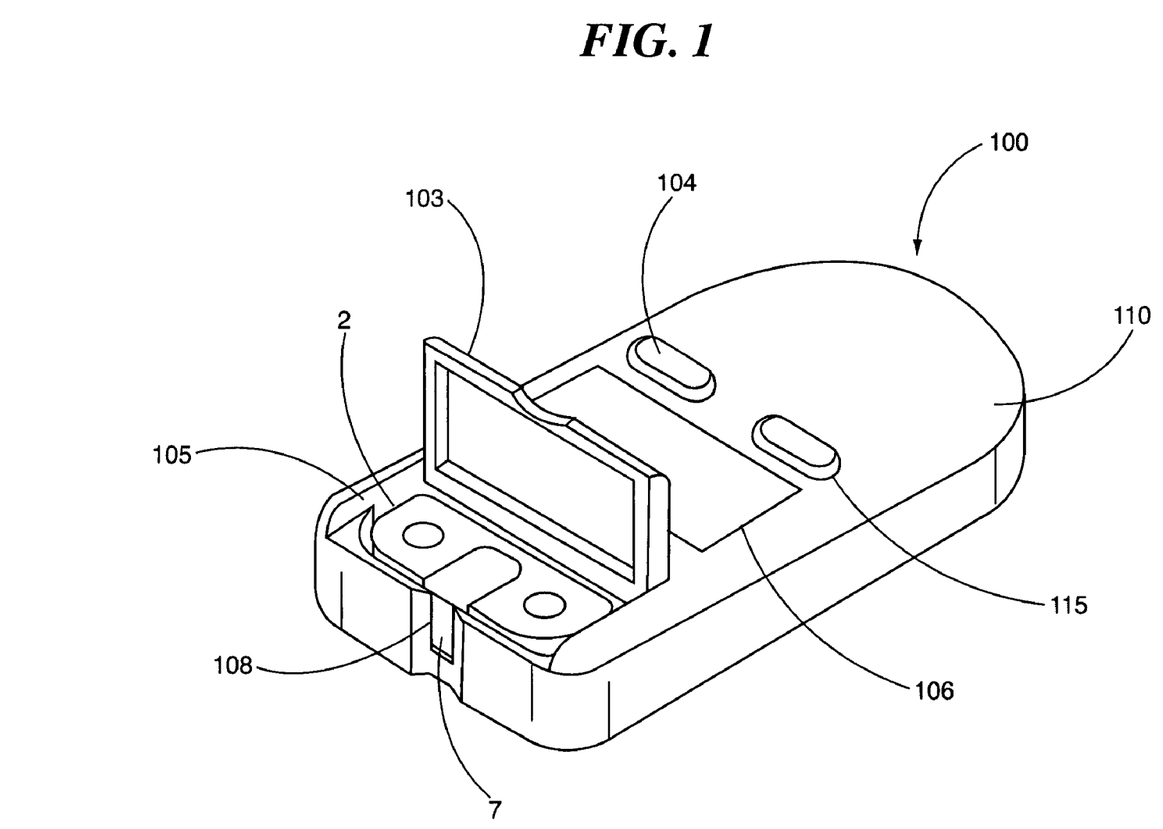
FIG. 1 is a perspective view showing an embodiment of a test tape cassette dispensing and an analysis device in accordance with the present invention.
Figure 2:
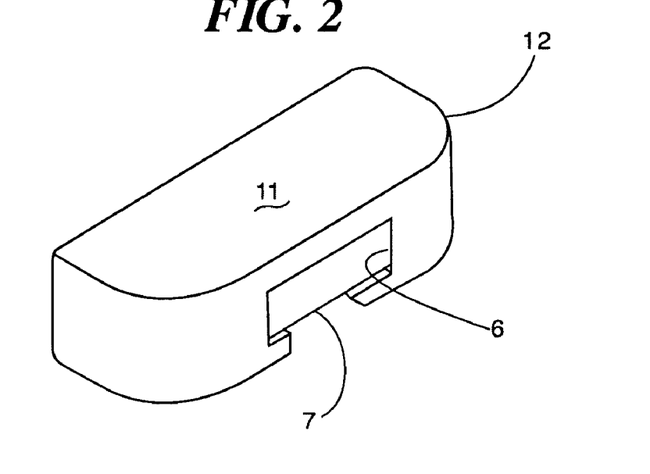
FIG. 2 is a perspective view showing an embodiment of the disposable test tape cassette in accordance with the present invention.
Figure 3:
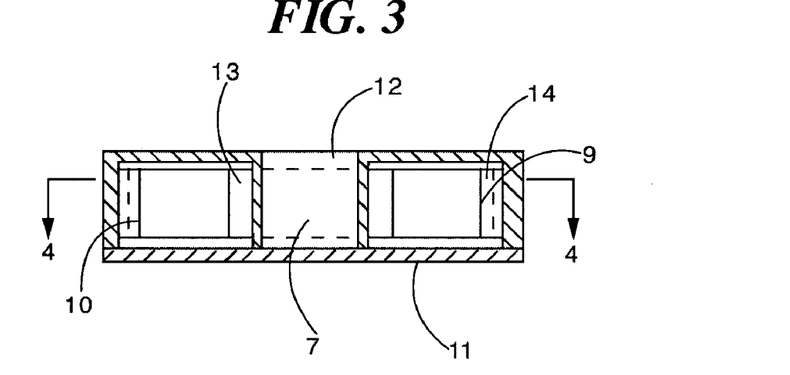
FIG. 3 is a sectional view of the test tape cassette taken along line 3-3 of FIG. 4.

Referring now more specifically to FIG. 1, which shows a blood glucose test tape cassette dispensing and analysis device embodying the present invention. The test tape cassette dispensing and analysis instrument 100 is a hand-held device which includes a housing 110 with ON/OFF 104 and memory/control buttons 115 as known in the art. A test tape housing area 105 is formed in housing 110. A hinged door 103 is mounted on the upper side of the housing capable of selectively opening or closing the test tape cassette housing area 105. Housing area 105 is sized, oriented and shaped to receive and operatively retain a cassette 2 therein in operative relationship to a test head (not shown) mounted within housing 110. A liquid crystal display window 106 is disposed on housing 110 to display messages and analysis test results. Housing 110 includes an aperture 108 providing access to cassette 2 when disposed within tape housing area 105.

In this test position, the test tape 7 is disposed between aperture 108 and the sensor head located adjacent to it. The sensor head is connected to electronic circuitry present onboard the dispensing and analysis device 1 capable of determining the presence of the analyte as known in the art. With the hinged door 103 in the open position, test tape cassette 2 is slid down in a vertical motion within tape housing area 105 to provide access to cassette 2 through door 103 or aperture 108.

Figure 4:
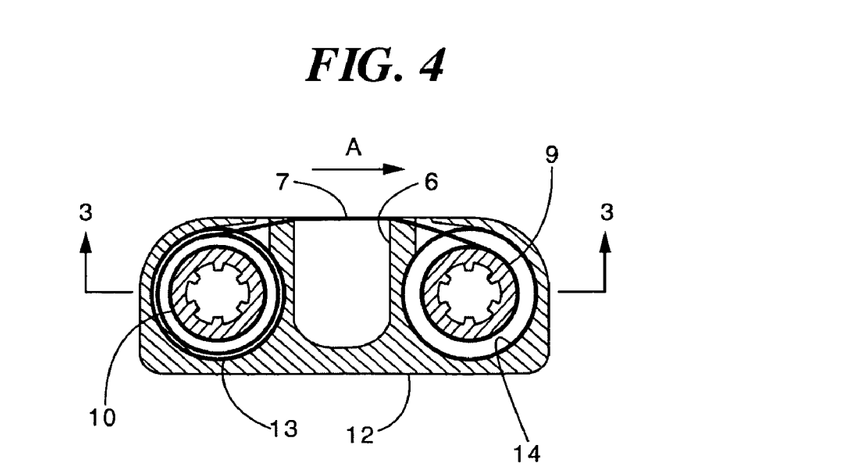
FIG. 4 is a sectional view of the test tape cassette taken along line 4-4 of FIG. 3.
Figure 5:
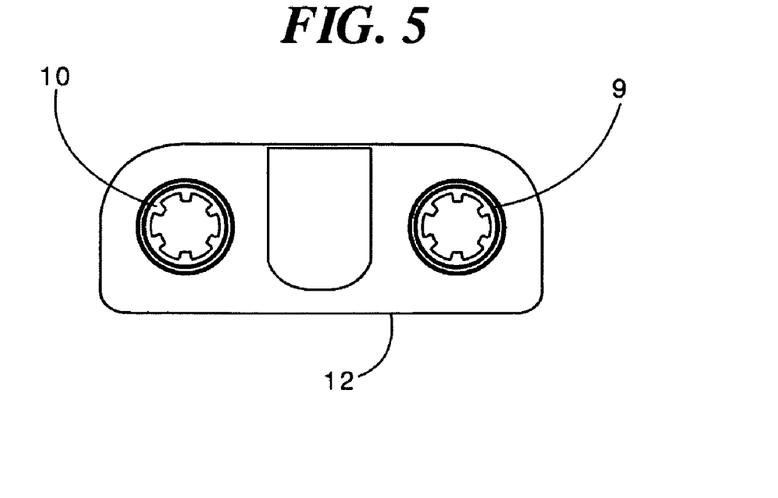
FIG. 5 is a top plan view of the test tape cassette.
Figure 6:
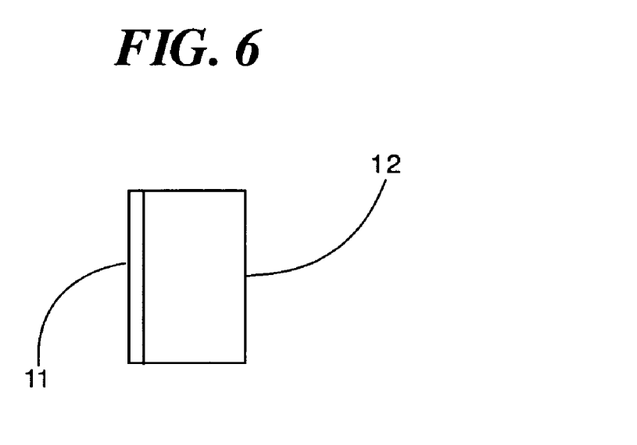
FIG. 6 is side elevational view of the test tape cassette.
Figure 7:
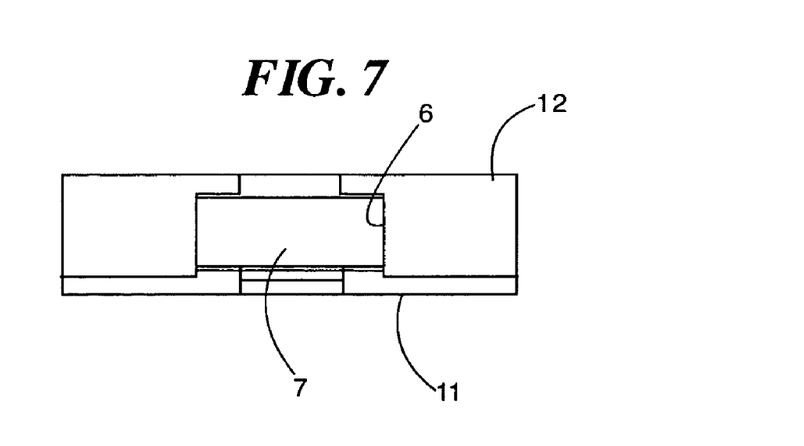
FIG. 7 is a front elevational view of the test tape cassette.
Figure 8:
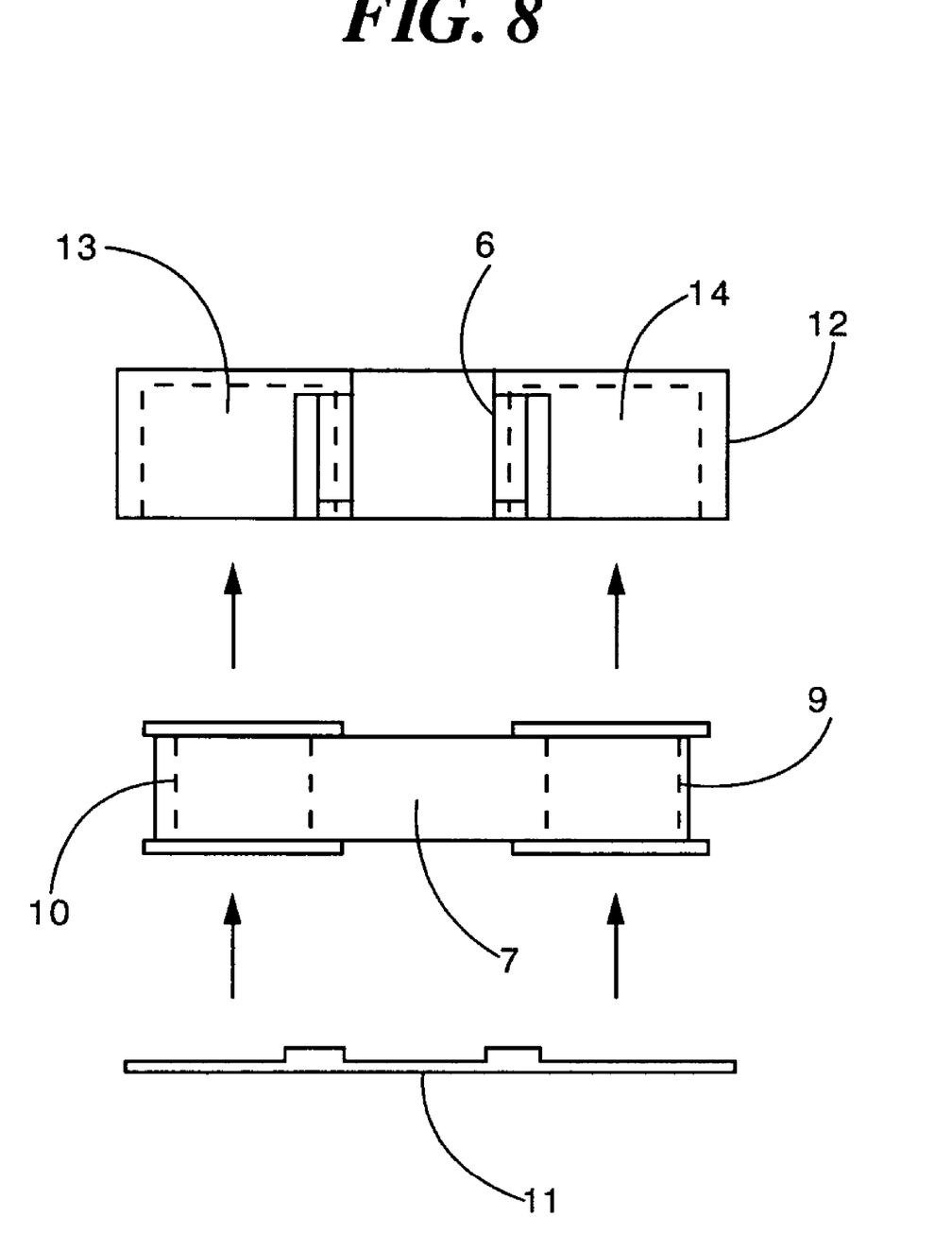
FIG. 8 is an exploded view of the cover, spools and casing of the test tape cassette constructed in accordance with the present invention.

Reference is now made to FIGS. 2-8. Test tape cassette 2 includes a test tape case 12 and a cover 11 providing a sealed housing for sealing tape 7 therein. Test tape cassette 2 is formed with an aperture 6 formed therein. Case 12 includes a first chamber 13 formed therein and a second chamber 14 formed therein. Chamber 13 and chamber 14 being separated by aperture 6. A take-up spool 9 may be disposed in chamber 14 and a feeding spool 10 may be disposed in chamber 13. When used, test tape 7 is disposed on and between spools 9, 10. Test tape 7 traces a path from chamber 14 and feeding spool 10 across aperture 6 onto take-up spool 9 in the direction of arrow A (FIG. 4). In a preferred embodiment, spools 9,10 are geared or teethed wheels which, when test tape cassette 2 is placed within tape housing area 110, engage drive shafts (not shown) of analysis device 10 so that the driving of drive shafts causes stepped rotation, and in turn stepped movement of test tape 7, the drive shafts may be a motor driven structure extending into tape housing area 105 which may be either manually or motor driven.

The unused portion of the continuous band of the test tape 7 is housed within the first chamber 13 of the test tape cassette 2 (FIGS. 2-8) and in a preferred exemplary embodiment is wound about a spool 10. A second spool 9 located in a second chamber 14 of the test tape cassette 2 and in a preferred embodiment is poised to receive the used portion of the test tape 7. It should be noted that, in a contemplated embodiment, tape 7 may be partially wound about spool 9 to start. The clockwise movement of spool 9 in the second chamber 14 actuates the movement of the test tape 7 from the first chamber 13 across gap 6 to the used second chamber 14. This continues in small increments, prior to each measurement made, until the unused portion of the test tape 7 is exhausted.

The test tape cassette housing 2 may be made of any rigid material, but is preferably made from ordinary moldable plastic types and consists of two parts that are adhered together by any of commonly used methods such as heat bonding or adhesives. Case 12 makes up the body and the sides of the housing and cover 11 is of such dimensions as to fit properly onto the case 12 and thus hermetically seals the two chambers 13,14. The first chamber 13, in addition to containing the unused portion of the test tape 7, may contain an adequate amount of desiccant material in order to maintain the unused test tape desiccated and in chemically reactive state for proper testing.

It should be also noted that in this embodiment spools 9,10 are used to draw tape 7 along a tape path. However, it should be noted that other drive structures for pulling a tape may be used and in fact it may be necessary only to use a single spool. By way of example, either of chambers 13, 14 may be used to house either the unused or used tape and the drive system would only be disposed in a respective other one of chambers 13, 14. For example, if spindle 10 were eliminated, take-up spool 9 could be powered to pull tape 7 across gap 6 through the test zone. A predetermined amount of tape 7 could be stored, either rolled about an axis without a spindle structure or neatly bunched within the room provided by chamber 13. In this way, the volume taken up by spindle 10 could be used to store even more of tape 7. Conversely, spindle 9 could be removed so that tape 7 is fed into chamber 14 by spindle 10 "pushing" tape 7 along the path. Furthermore, either one of spindles 9, 10 can be driven either manually through a crankshaft or knob, mechanically cooperating with a respective spindle or by a motor operatively engaged with either one of the spindles; the motor being mounted within housing 110 and under control of any of the buttons on housing 110.

Figure 9A:
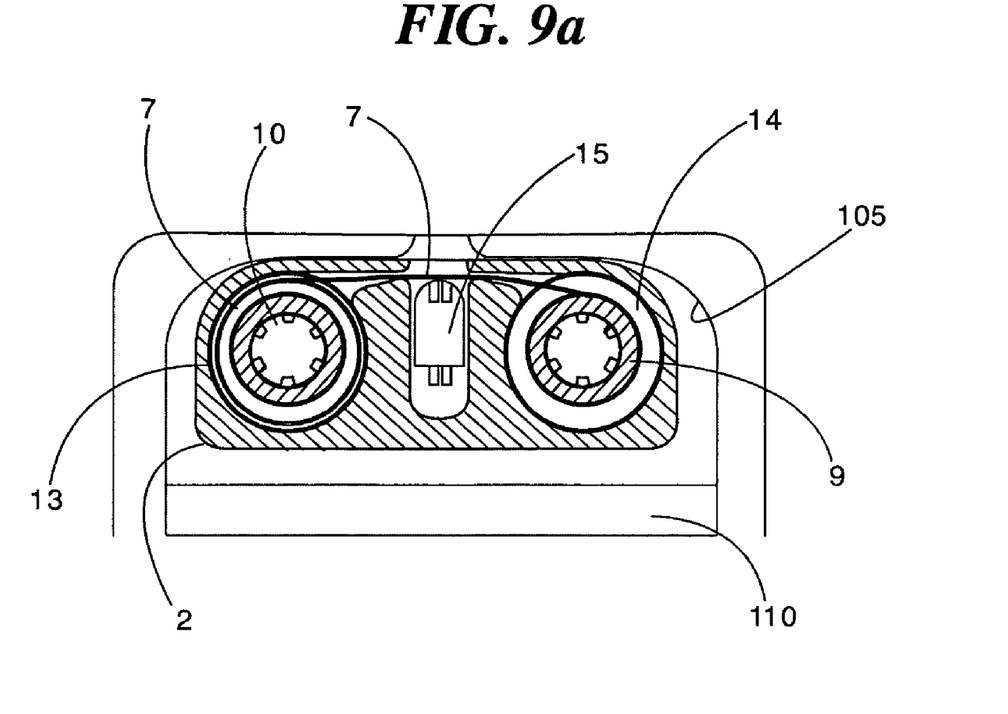
FIG. 9a is a top plan view of the test tape cassette disposed within the analysis device shown in FIG. 1 wherein the sensor head is retracted.
Figure 9B:
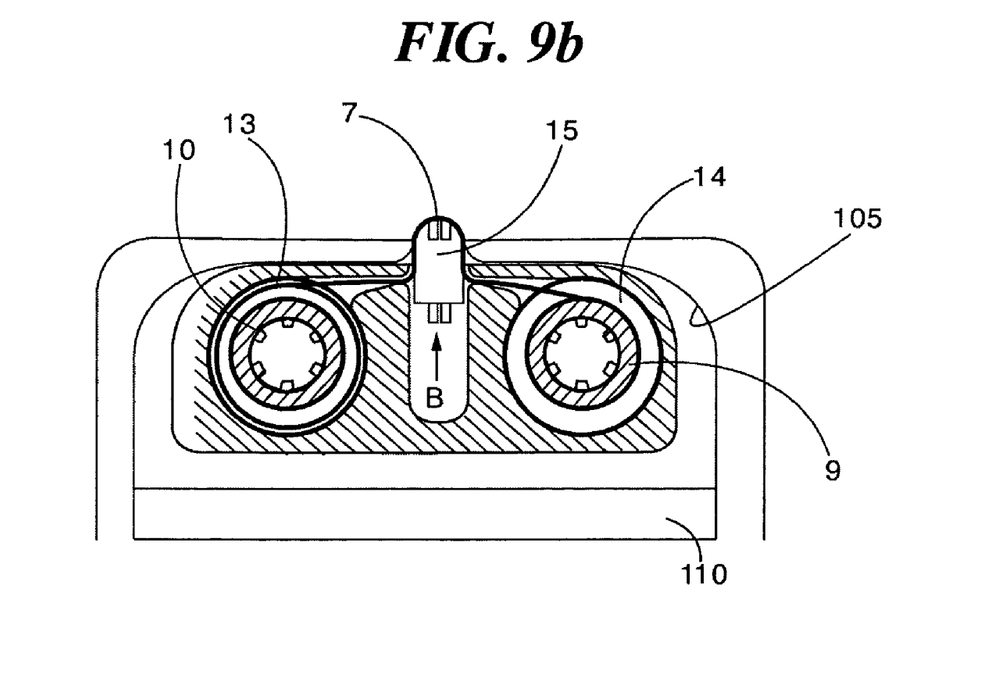
FIG. 9b is a top plan view of the test tape cassette disposed within the analysis device shown in FIG. 1 wherein the sensor head is in test position.

In a preferred embodiment of the present invention, a sensor head 15 is moveably mounted within housing 100 (FIGS. 9a-9b) In an embodiment using an electrode sensor, sensor head 15 is in a retracted position when the dispensing device 100 is in the OFF mode. In order to make a sample measurement the sensor head 15 is elevated into a TEST position. As sensor head 15 is moved to the TEST position in the direction of arrow B, it draws a fixed length of the unused portion of the test tape 7 through aperture 108 of the dispensing and analysis device 100 and exposes the test tape 7 to the environment. In this position, test tape 7 is now in the ready mode to accept a small sample of test fluid for testing.

In the preferred embodiment of the present invention, the test tape is composed of a plurality of active zones, each including at least two layers of material with a small gap between the layers at the active zone allowing a small volume of the fluid sample to seep in between the layers and filling the gap. In such an embodiment, the fluid sample may be introduced from the side of the test tape 7. In a separate embodiment of the present invention the test tape 7 is constructed such that a small volume of the fluid sample is introduced from the top of the test tape 7. Both of these embodiments are described below.

Figure 13:
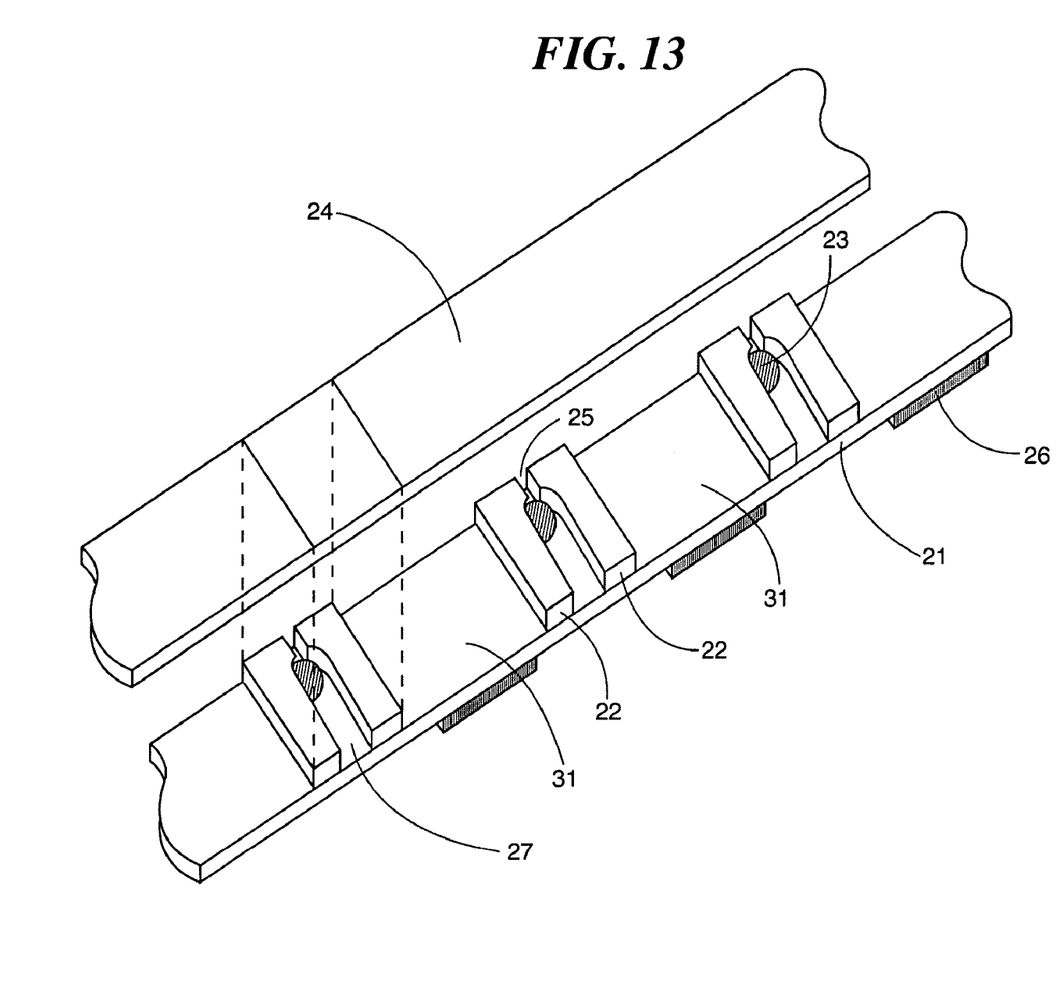
FIG. 13 is an exploded perspective view of yet another embodiment of the test tape constructed in accordance with yet another embodiment of the present invention.

Reference is now made to FIG. 13, which depicts the preferred embodiment of the improved, multi-layered diagnostic test tape 7 of the instant invention is poised to laterally accept a small fluid sample. The test tape 7 represents an improvement over test strips designed and manufactured previously and described in the literature, whereby it contemplates the novel features that make the strip tape 7 easier and safer to use, whereby a whole blood sample from a finger stick, or otherwise, is applied to the test tape 7 to determine the amount of an analyte, e.g., glucose, or other analytes of interest such as cholesterol, alcohol and others.

As shown in FIG. 13, tape 7 generally includes a cover layer 24 and a lower support layer 21. A plurality of active zones 27 is disposed along tape 27 between lower support layer 21 and cover layer 24. A separating member 22 generally in the shape of a U, by way of example, in the preferred embodiment is disposed between layers 21,24. In this embodiment, each active zone 27 is defined by the gap within a separating member 22. In a preferred embodiment, active zone 27 may be formed by two close spaced separating members 22 between consecutive separating of test tape 7. A cleansing member 26 is placed on the opposed surface of support layer 21 from separating members 22. Cleansing members 26 are intermittently disposed between active zones 27. A gap h in between adjacent separating members 22 at active zones 27 defines a sample receiving port to permit the introduction of the sample to the active zone 27. A reagent 23 is disposed on support layer 21 within each active zone 27.

Figure 11:
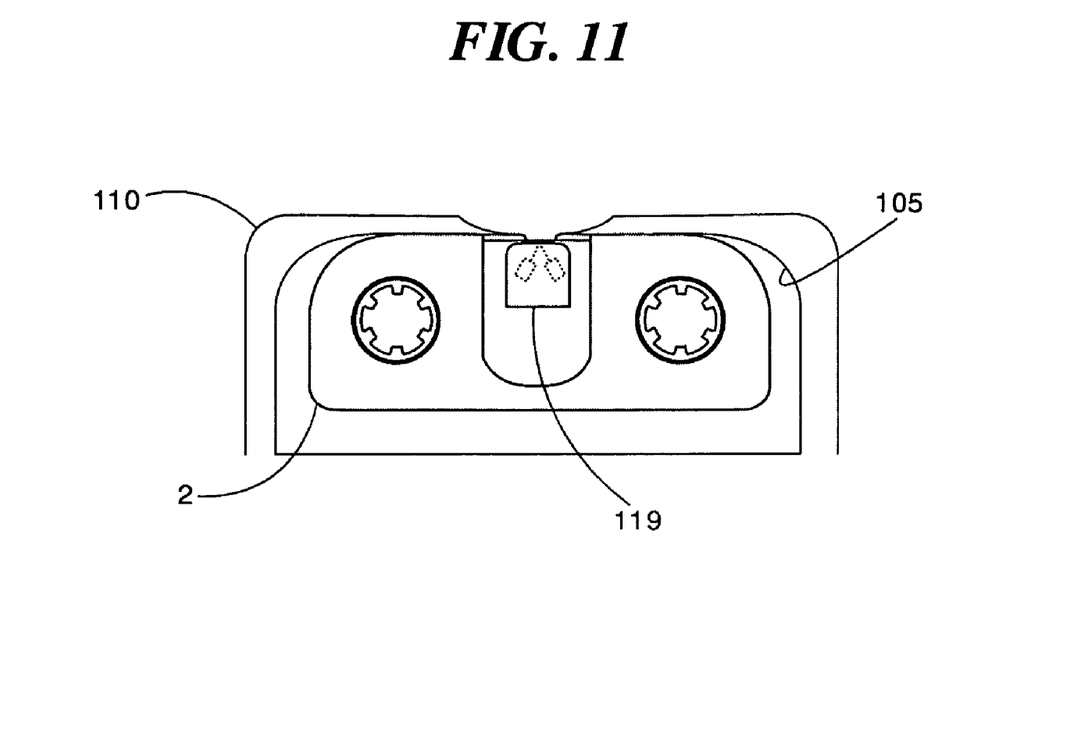
FIG. 11 is a top plan view of a test tape cassette dispensing and analysis device incorporating a photo sensor head.

In a preferred non-limiting embodiment, a narrow venting slit 25 is formed at one end of gap h between separating member 22, interconnecting the area of the active zone 27 to the outside of test tape 7, allowing free flow of air from the inner area of active zone 27 to the outside, and therefore preventing formation of any air bubbles upon the introduction of the sample to the test area. This allows the sample received by the test tape 7 to pass directly from the sample receiving port of active zone 27 to the opposite side, thereby completely filling active zone 27 with the sample material. Upon completion of the sample fill, the chemical reaction between the analyte of interest and the appropriate reagent matrix 23 present in active zone 27 is initiated, generating a color change or an electrochemical reaction end product. A sensor head 19 or 15, disposed in housing 100 (see FIGS. 9A, 9B, 11) below active zone 27 is capable of monitoring these changes, either a color change or an electrochemical change, respectively.

Upon completion of each single test and analysis of a particular fluid sample, the test tape 7 is moved a fixed distance in the direction of arrow A (FIG. 4) allowing the unused portion of the test tape 7 to come into the next test position by placing the next unused active zone 27 between aperture 108 and sensor head 15 or 19 with active zone 27 facing towards aperture 108. In the case of the electrochemical mode of testing, sensor head 15 is in direct and physical contact with test tape 7 above. Therefore, the forward movement of test tape 7 causes layer 26 to contact sensor head 15 to clean sensor head 15. In the optical mode of the testing, sensor head 19 need not be in physical contact with test tape 7 at any time during or after a test protocol and cleaning layer 26 is not necessary.

As noted above, the area between respective pairs of members 22 defines the active zone 27 of test tape 7 wherein a matrix including reagent 23 is present. The support layer 21 is pretreated with reagent matrix 23 generally in the form of a dry chemistry mix. All the layers present in test tape 7 may be laminated or placed tightly next to each other by means of appropriate glue, heat welding, pressure, or ultrasonic welding and bonding. Furthermore, separating member 22 may be formed as a single closed U, separated parallel bars or any other shape which separates layer 21 from 24, while defining an area for deposit of an analyte to cause a reaction to occur with reagent 23.

The support layer 21, cover layer 24 and the separating members 22 may be constructed from the same or different material of any chemical composition readily available, including, but not limited to, those of, generally flexible plastic or polymeric material such as Mylar, vinyl, polystyrene, polyester, polycarbonate, polyethylene and polypropylene or similar material. Furthermore, the support layer 21 may be in solid or woven mesh form; clear or opaque form.

The reagent matrix 23 of the subject invention is bound to the support layer 21 by any one of adsorption, absorption, covalent and or non-covalent binding, and contains typically, by way of non-limiting example, an oxidase enzyme which is capable of producing hydrogen peroxide from the analyte. For the optical method of detection the reagent matrix 23 typically will contain a second enzyme, particularly a peroxidase and a chromogenic dye system, which produces a change of color due to the enzymatic activity of the peroxidase. The hydrogen peroxide can then react with a dye intermediate or precursor, to produce an oxidized form of the intermediate or precursor. This oxidized material may produce the colored product or react with a second precursor to form the final dye. This change in color intensity or dye absorbance may be determined by measuring the change in the absorbance of the test sample between two or more points in time and is related to the amount of the analyte in the fluid sample.

Typical examples of a reagent composition may include, by way of non-limiting example, the following: Glucose Oxidase and a Peroxidase (e.g., horseradish peroxidase) and any of the following Oxygen Acceptors: e.g., o-toluidine, o-dianisidine, o-tolidine, 3-Methyl-2-benzothiazolinone hydrazone plus N,N-dimethylaniline, or Phenol plus 4-aminophenazone, and others well known in the prior art.

The optional electrochemical method of detection also typically involves an oxidase enzyme, which is capable of producing hydrogen peroxide. However, the electrochemical method would in the preferred embodiment require a mediator, such as potassium ferricyandie. The reagent matrix 23 may include other components for particular applications, such as stabilizers, fillers and/or enhancers, including buffering materials, binders, and surfactants, commonly known and described in the prior art. The glucose oxidase oxidizes the glucose to gluconic acid and at the same time the mediator ferricyanide is reduced to ferrocyanide, which in the presence of an appropriate voltage bias between the two electrodes causes a current to be generated in proportion to the amount of glucose present in the fluid sample. The reagent will be in a matrix to which reagents may be covalently or non-covalently bound. Examples of matrix surfaces are hydrophilic porous polyamides, which allow for the free flow of an aqueous medium through the matrix. It will also allow for binding of the required enzymes to the matrix and thereby immobilizing said enzymes in the active zone without affecting their enzymatic activities.

The methodology for the determination of the analyte, such as glucose, involves the application of a small volume of blood to the reagent matrix 23 present in active zone 27 which in time results in the change of color, or change in the light absorption/transmission properties of the test tape 7 at active zone 27, or production of an electrochemical signal detectable by the sensor head just below the test tape 7. Typically, after the addition of a small volume of blood to active zone 27 of the test tape 7, a reading is taken at fixed time intervals, typically one second apart, as many times as necessary, as a measure of the formation of the product in proportion to the amount of analyte present in the sample. The change in the amount of enzymatic end product as detected by the sensor over the time period is then related to the amount of the analyte present in the sample.

Figure 14:
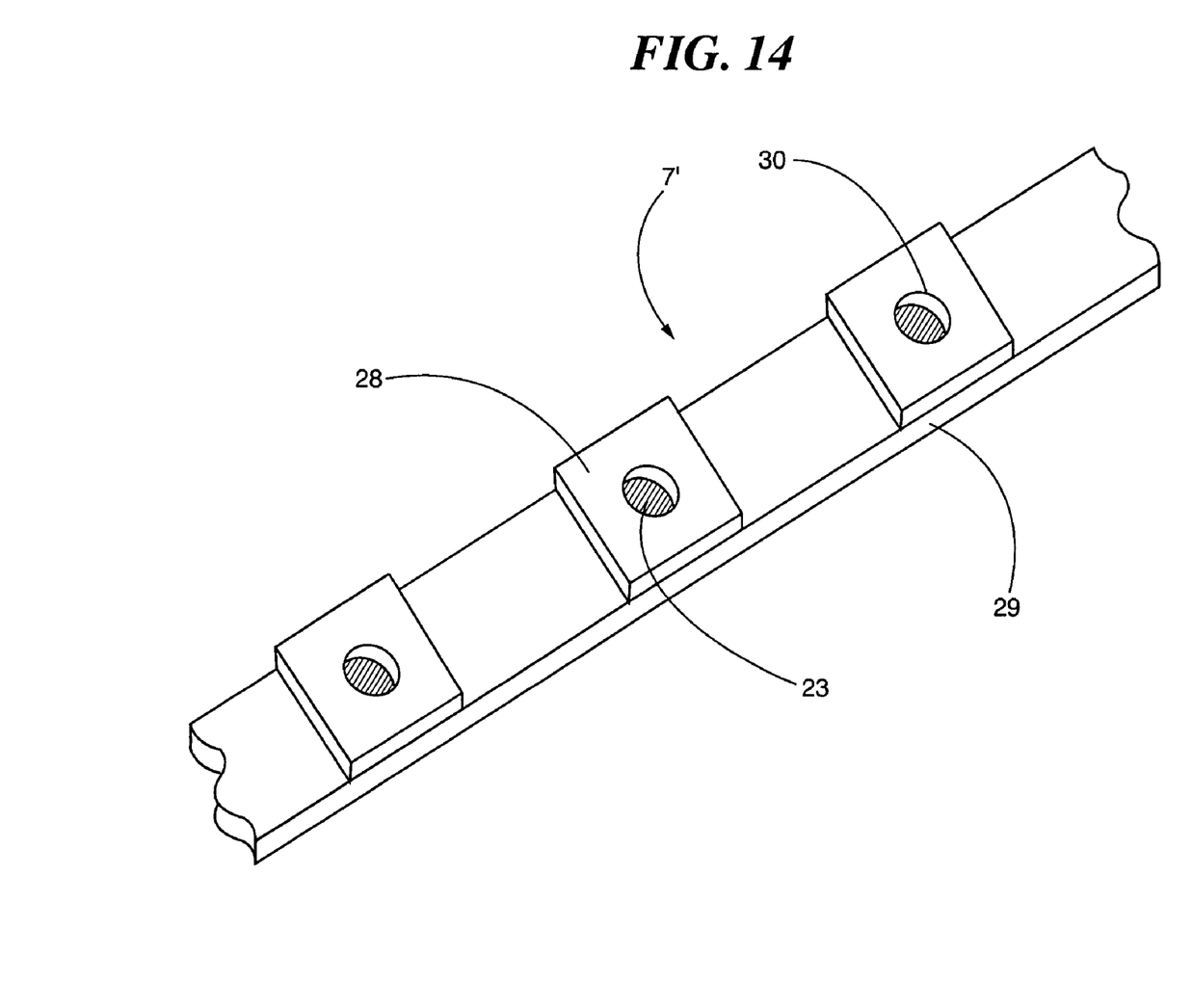
FIG. 14 is a perspective view of yet another embodiment of the test tape constructed in accordance with the present invention.

In a separate embodiment of the present invention as shown in FIG. 14, test tape 7 is depicted to enable receiving a small volume of fluid sample from the top of the test tape 7, and comprises a support layer 29. A holding member 28 is embedded or attached to support layer 29 at spaced intervals (preferably equal distances). Holding member 28 includes a cavity 30 in its center for the purpose of receiving and holding a small volume of the test fluid. A reagent matrix 23 is disposed within cavity 30 to form active zone 27. This construct enables the introduction of a small volume of fluid sample, e.g. whole blood directly onto cavity 30 and thereby filling the cavity therein. A chemical reaction is then initiated by the interaction of the analyte present in the fluid sample and reagent matrix 23 present in active zone 27 of test tape 7. Typically, after the addition of a small volume of blood to active zone 27 of test tape 7, a reading is taken at fixed time intervals as many times as necessary, as a measure of the formation of the product in proportion to the amount of analyte present in the sample. The change in the amount of enzymatic end product as detected by the sensor over the time period is then related to the amount of the analyte present in the sample.

Figure 10:
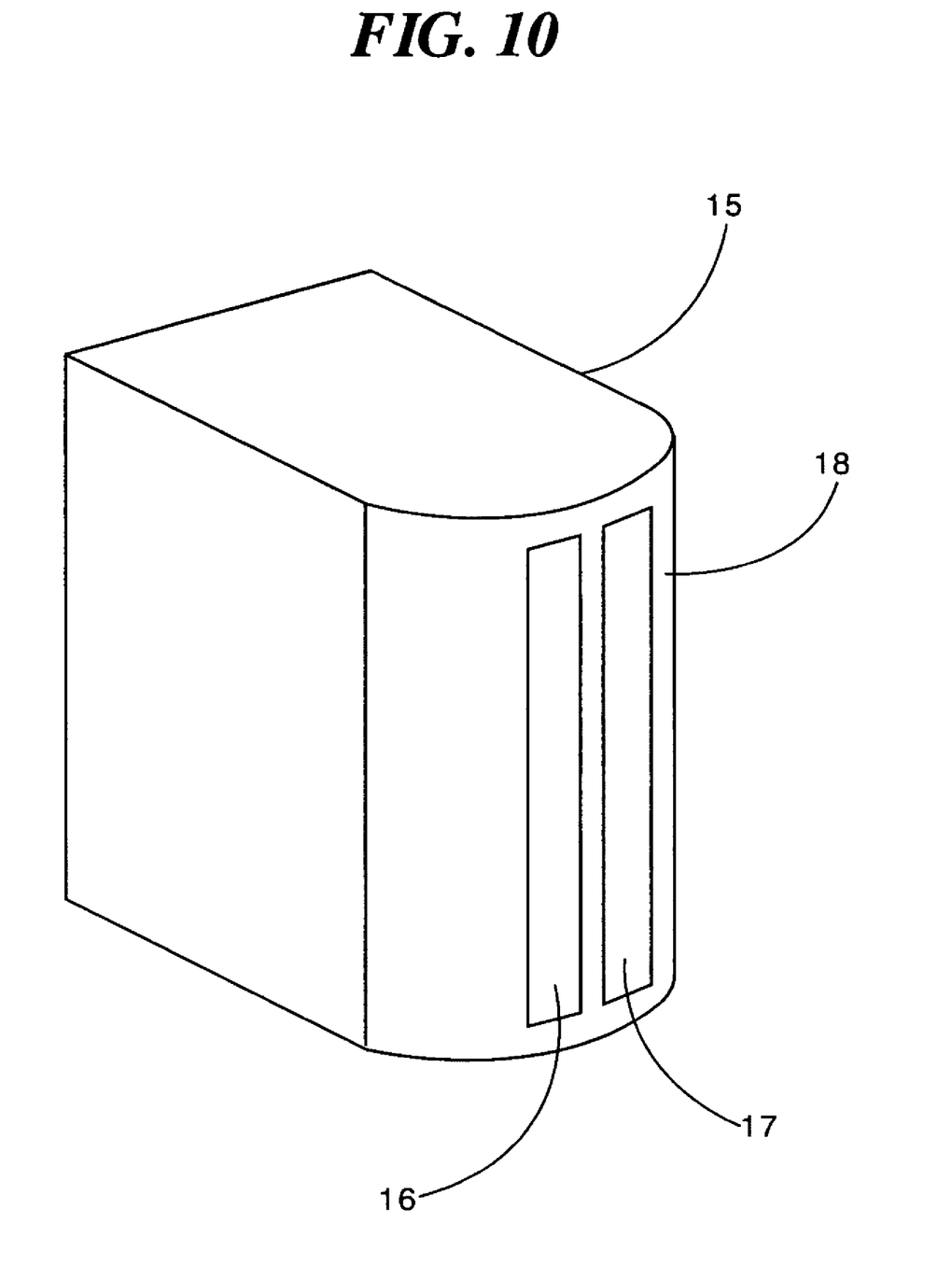
FIG. 10 is a perspective view of an electrochemical sensor head.

An electrode based sensor head 15 (FIG. 10) utilized in the preferred embodiment of the present invention to sense chemical reactions in the sample includes an insulating housing 18. At least two electrodes 16,17, for example, made of gold, platinum, silver, silver-chloride, carbon, steel, and alloys or mixtures of same or other metals are bonded, painted, printed, or embedded within or onto the surface of the insulating housing 18. Insulating housing 18 may be made from any common electrically insulating material, such as glass, plastic or similar polymeric and dielectric non-conducting materials by way of example. Electrodes 16,17 are physically and electrically connected with circuitry present in analysis device 100, as is known in the art, and carry electrical signals from active zone 27 of the test tape to the device 100.

In yet another embodiment of the present invention, sensor head 119 (FIG. 11) is of optical type, capable of emitting and receiving light at different wavelengths and thus measuring color intensity or other optically measurable changes from the test tape 7 as is known in the art.

Figure 15:
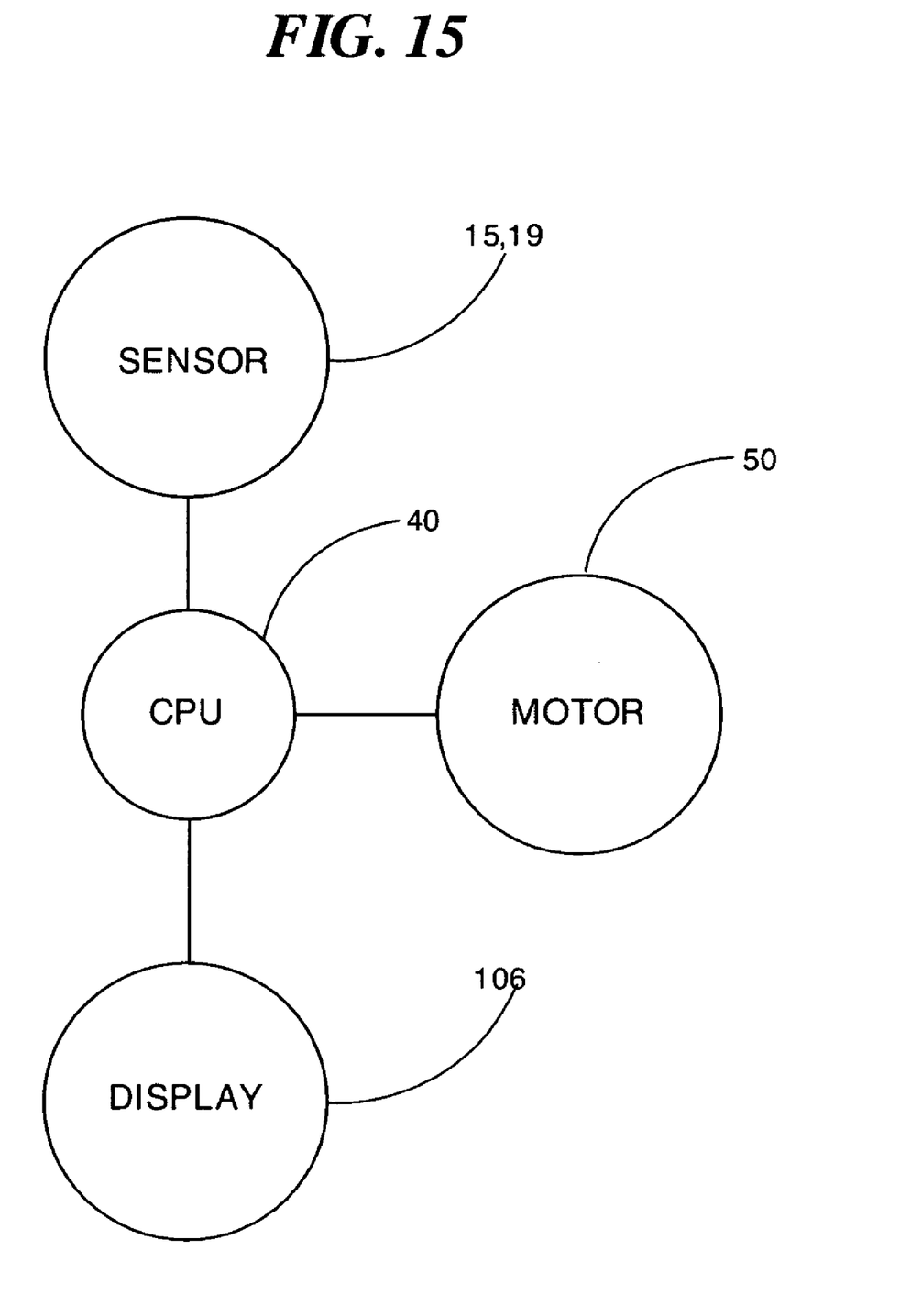
FIG. 15 is a schematic view of the control structure of yet another embodiment of an analysis device constructed in accordance with the present invention.

In the preferred embodiment of the present invention the cassette dispensing and analysis device may be run under computer control. Mounted within the housing 110 is a CPU 40 (FIG. 15), which is coupled to sensor 15, or sensor 19, for receiving and interpreting the information and driving display 106 to display the test results. Furthermore, CPU 40 may also drive a motor 50 coupled to take-up spool 9 for selectively advancing test tape 7 in response to control buttons 105.

Figure 12:
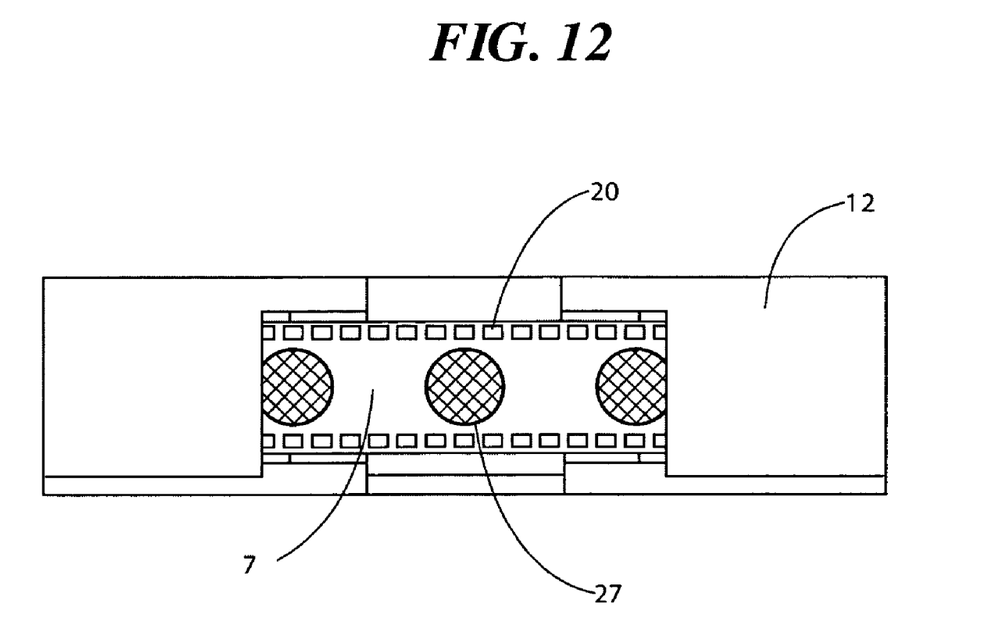
FIG. 12 is a front elevational view of the test tape located in the cassette housing incorporating sprocket alignment holes in accordance with another embodiment of the invention.

As seen in FIG. 12, a test tape 7 may include sprocket alignment holes 20 allowing for coupling of test tape 7 with sprockets present on take-up spool 9 and causing a forward motion while preventing tape slippage. In addition, sprocket holes 20 may aid in the proper alignment of test tape 7 with sensor head 15 or 19. Furthermore, in a preferred embodiment, the used tape 7 is taken up on take-up spool 9, which may be operated either manually or by motor 50. However, spool 9 is only used by way of example and a take-up arm, tension drag device or other sliding mechanism or other take-up devices as known in the art may be utilized.

Reference is again made to FIGS. 1, 13 and 14 in which operation of the invention is provided. Cassette dispensing and analysis device 100 is generally in the OFF mode. Prior to making of a measurement of a fluid sample the dispensing and analysis device 100 is put in the ON mode which in turn activates all electronics circuitry and in addition causes the advancement of a predetermined segment of test tape 7 in the forward direction sufficient to position active zone 27 of test tape 7 in the test region which is located in the aperture 108. This step is followed by the physical lifting of test tape 7 by sensor head 15 as it moves in the direction of arrow B through aperture 108 and causes the protrusion of the test segment of test tape 7 through aperture 108. Test tape 7 is now exposed and available for receiving a small drop of fluid sample such as whole blood. The dispensing and analysis device 100 is now considered to be in the SET mode, cassette 2 is now set to accept a fluid sample for measurement. During the TEST mode, a sample fluid, for example, a drop of blood either from a finger prick or from a capillary tube, is delivered to the test region of test tape 7 at aperture 108. This step, in turn, marks the beginning of the test cycle and the dispensing and analysis device 100 begins the collection of data from the electrodes located in sensor head 15. After a predetermined period of time, data collected is converted into meaningful numbers as is known in the art and shown on the liquid crystal display readout 106.

After the test cycle is completed and a readout obtained, a predetermined segment of the test tape is advanced in the direction of arrow A causing the cleaning and/or cleansing of the electrochemical electrodes and the sensor head by cleansing member 26 of test tape 7 along sensor head 15. In the present invention, the chemical composition of the cleaning/cleansing material embedded, adsorbed or absorbed in layer 26 of test tape 7 may include, but is not limited to, surfactants, proteins, enzymes, salts, polymeric components and other additives as required for dissolution, cleaning and/or cleansing of the sensor surfaces in preparation for the following cycle of analyte measurement. When this cleaning and/or cleansing cycle is completed, sensor head 15 is retracted to its original lower position, followed by the movement of the used portion of test tape 7 to the second chamber 14 of test tape cassette 2 for storage. Measurement and analysis device 100 is put in the OFF mode once again. It should be noted that in non-preferred embodiments that the lands 31 between separating layer pairs 22 could be used to wipe sensor head 15 clean as tape 7 passes over sensor head 15. Furthermore, sensors 15, 19 need not move through cassette 2, they need only be positioned sufficiently close to detect the results.

In a separate embodiment of the present invention, test tape 7 is in physical contact with electrochemical sensor head 15 at all times, and there is no requirement for the sensor head to move in a vertical or any other direction. And, in yet another embodiment of the present invention, the sensor head 19 is of optical nature and is located in the close proximity of test tape 7 and is not in physical contact with test tape 7.

In summary, the system of the present invention provides numerous advantages over prior art. First, operator time and effort is kept to a minimum and is limited to initial loading of the test tape cassette, followed by application of a small amount of fluid sample to the active zone of the test tape for a given test, thus eliminating the need for retrieval of a separate test strip followed by the loading of same onto the device. Second, at the completion of the test, there is no requirement for the safe disposal of the spent test strip, thereby eliminating a step typically required by all previous teachings. Third, there is no need to carry a separate container of test strips. Fourth, the construction of the test tape generally requires fewer parts and components, and, therefore, provides an opportunity to manufacture a lower cost system for the use by diabetics.

While the invention has been described with reference to details of the illustrated embodiment, these details are not intended to limit the scope of the invention as defined in the appended claims. The device can be used in connection with fluid analysis of any type of fluid including but not limited to, biological, chemical, environmental or industrial; and furthermore the device can be utilized to analyze any analyte in these fluid samples, including glucose and other analytes as well, by means of appropriate choice of reagent material commonly known to those skilled in the arts.

The invention claimed is:

1. A biochemical analysis instrument for multiple fluid analyses includes:
    a housing;
    a sensor for sensing a reaction disposed in said housing;
    an aperture formed in said housing;
    a test tape housing area formed in said housing, said sensor being disposed to selectively move within said housing area, said aperture being formed to provide access to said tape housing area; and
    a cassette configured to be received within said tape housing area; said cassette including a case, a first chamber formed in said case, a second chamber formed in said case, a gap formed in said case, said first chamber and second chamber being disposed at a respective side of said gap, a test tape disposed within said housing extending from said first chamber across said gap to said second chamber, said test tape having a plurality of active zones disposed at predetermined spaced intervals along said tape for testing an analyte; said active zone including a reagent disposed on said test tape at said active zone;
    said test tape including a support layer; and each active zone including at least a first separating member and a second separating member, said first separating member disposed on said support layer across a gap from a second separating member disposed on said support layer; a reagent disposed within said gap between said first separating member and said second separating member; and said first separating member and said second separating member together are substantially U-shaped; and a venting slit separating said first separating member from said second separating member.

2. A biochemical analysis instrument for multiple fluid analyses includes:
    a housing;
    a sensor for sensing a reaction disposed in said housing;
    an aperture formed in said housing;
    a test tape housing area formed in said housing, said sensor being disposed to selectively move within said housing area, said aperture being formed to provide access to said tape housing area; and
    a cassette configured to be received within said tape housing area; said cassette including a case, a first chamber formed in said case, a second chamber formed in said case, a gap formed in said case, said first chamber and second chamber being disposed at a respective side of said gap, a test tape disposed within said housing extending from said first chamber across said gap to said second chamber, said test tape having a plurality of active zones disposed at predetermined spaced intervals along said tape for testing an analyte; said active zone including a reagent disposed on said test tape at said active zone;
    said test tape including a support layer; and each active zone includes at least a first separating member and a second separating member, said first separating member disposed on said support layer across a gap from a second separating member disposed on said support layer; a reagent disposed within said gap between said first separating member and said second separating member; and said tape having a cover layer, said first separating member and said second separating member being disposed between said support layer and said cover layer.

3. A biochemical analysis instrument for multiple fluid analyses includes:
    a housing;
    a sensor for sensing a reaction disposed in said housing;
    an aperture formed in said housing;
    a test tape housing area formed in said housing, said sensor being disposed to selectively move within said housing area, said aperture being formed to provide access to said tape housing area; and
    a cassette configured to be received within said tape housing area; said cassette including a case, a first chamber formed in said case, a second chamber formed in said case, a gap formed in said case, said first chamber and second chamber being disposed at a respective side of said gap, a test tape disposed within said housing extending from said first chamber across said gap to said second chamber, said test tape having a plurality of active zones disposed at predetermined spaced intervals along said tape for testing an analyte; said active zone including a reagent disposed on said test tape at said active zone;
    said test tape including a support layer; and each active zone including at least a first separating member and a second separating member, said first separating member disposed on said support layer across a gap from a second separating member disposed on said support layer; a reagent disposed within said gap between said first separating member and said second separating member; and a cleansing member, said cleansing member being disposed between respective adjacent active zones.

4. The instrument of claim 3, wherein said cleansing member extends from said support layer from a surface of said support layer which is the opposed surface to a surface of said support layer which supports said separating members.

5. The instrument of claim 2, wherein said tape further comprises lands disposed between adjacent pairs of said separating members.

6. The instrument of claim 2, further comprising a spool disposed in at least one of said first chamber and second chamber, and said tape further comprising sprocket alignment holes disposed along at least one edge of said tape for engagement with said spool, said tape traveling along a travel path within said cassette from said first chamber to said second chamber and being wound about said spool.

7. The instrument of claim 6, wherein said path traverses said gap in said casing to selectively expose each active zone to an analyte.

8. The instrument of claim 2, wherein said reagent includes an enzyme, said reagent causes a changing of color when the analyte is a targeted analyte.

9. The instrument of claim 2, wherein said reagent includes an enzyme, said reagent causes a reaction which generates an electrochemical signal when the analyte is a targeted analyte.

10. A biochemical analysis cassette comprising:
a case;
a first chamber formed in said case;
a second chamber formed in said case, a gap formed in said case, said first chamber and second chamber being disposed at a respective side of said gap;
a test tape disposed within said case extending from said first chamber across said gap to said second chamber, said test tape having a plurality of active zones disposed at predetermined spaced intervals along said test tape for testing an analyte, said active zone including a reagent disposed on said test tape at said active zone and wherein said test tape includes a support layer and each active zone includes at least a first separating member and a second separating member, said first separating member disposed on said support layer across a gap from a second separating member disposed on said support layer; and
a reagent disposed within said gap between said first separating member and said second separating member; said first separating layer and said second separating layer together are substantially U-shaped; and further comprising a venting slit separating said first separating member from said second separating member.

11. A biochemical analysis cassette comprising:
a case;
a first chamber formed in said case;
a second chamber formed in said case, a gap formed in said case, said first chamber and second chamber being disposed at a respective side of said gap;
a test tape disposed within said case extending from said first chamber across said gap to said second chamber, said test tape having a plurality of active zones disposed at predetermined spaced intervals along said test tape for testing an analyte, said active zone including a reagent disposed on said test tape at said active zone and said test tape including a support layer and each active zone including at least a first separating member and a second separating member, said first separating member disposed on said support layer across a gap from a second separating member disposed on said support layer; and
a reagent disposed within said gap between said first separating member and said second separating member; said tape including a cover layer, said first separating member and said second separating member being disposed between said support layer and said cover layer.

12. A biochemical analysis cassette comprising:
a case;
a first chamber formed in said case;
a second chamber formed in said case, a gap formed in said case, said first chamber and second chamber being disposed at a respective side of said gap;
a test tape disposed within said case extending from said first chamber across said gap to said second chamber, said test tape having a plurality of active zones disposed at predetermined spaced intervals along said test tape for testing an analyte, said active zone including a reagent disposed on said test tape at said active zone and wherein said test tape including a support layer and each active zone including at least a first separating member and a second separating member, said first separating member disposed on said support layer across a gap from a second separating member disposed on said support layer; and
a reagent disposed within said gap between said first separating member and said second separating member; said cleansing member being disposed between respective adjacent active zones.

13. The cassette of claim 12, wherein said cleansing member extends from said support layer from a surface of said support layer which is the opposed surface to a surface of said support layer which supports said separating members.

14. The cassette of claim 10, wherein said tape further comprises lands disposed between adjacent pairs of said separating members.

15. The cassette of claim 10, further comprising a spool disposed in at least one of said first chamber and second chamber, and said tape further comprising sprocket alignment holes disposed along at least one edge of said tape for engagement with said spool, said tape traveling along a travel path within said cassette from said first chamber to said second chamber and being wound about said spool.

16. The cassette of claim 15, wherein said path traverses said gap in said casing to selectively expose each active zone to an analyte.

17. The cassette of claim 10, wherein said reagent includes an enzyme, said reagent causes a changing of color when the analyte is a targeted analyte.

18. The cassette of claim 10, wherein said reagent includes an enzyme, and said reagent causes a reaction which generates an electrochemical signal when the analyte is a targeted analyte.

19. A biochemical analysis instrument for multiple fluid analyses includes:
a housing;
a sensor for sensing a reaction disposed in said housing;
an aperture formed in said housing;
a test tape housing area formed in said housing, said sensor being disposed to selectively move within said housing area, said aperture being formed to provide access to said tape housing area; and
a cassette configured to be received within said tape housing area; said cassette including a case, a first chamber formed in said case, a second chamber formed in said case, a gap formed in said case, said first chamber and second chamber being disposed at a respective side of said gap, a test tape disposed within said housing extending from said first chamber across said gap to said second chamber, said test tape having a plurality of active zones disposed at predetermined spaced intervals along said tape for testing an analyte; said active zone includes a reagent disposed on said test tape at said active zone; and a cleansing member, said cleansing member being disposed between respective adjacent active zones along said test tape.

20. The instrument of claim 19, wherein said test tape further comprises a support layer, said active zone and said cleansing members being disposed on said support layer, and said cleansing member extends from said support layer from a surface of said support layer which is the opposed surface to a surface of said support layer which supports said active zones.

21. A biochemical analysis instrument for multiple fluid analyses includes:
   a housing;
   a sensor for sensing a reaction disposed in said housing;
   an aperture formed in said housing;
   a test tape housing area formed in said housing, said sensor being disposed to selectively move within said housing area, said aperture being formed to provide access to said tape housing area;
   a cassette configured to be received within said tape housing area; said cassette including a case, a first chamber formed in said case, a second chamber formed in said case, a gap formed in said case, said first chamber and second chamber being disposed at a respective side of said gap, a test tape disposed within said housing extending from said first chamber across said gap to said second chamber, said test tape having a plurality of active zones disposed at predetermined spaced intervals along said tape for testing an analyte, said active zone includes a reagent disposed on said test tape at said active zone; and further includes a cleansing member, said cleansing member being disposed between respective adjacent active zones.

22. The instrument of claim 21, wherein said test tape further comprises a support layer, said active zone and said cleansing members being disposed on said support layer, and said cleansing member extends from said support layer from a surface of said support layer which is the opposed surface to a surface of said support layer which supports said active zones.

* * * * *